United States Patent
Miller

(10) Patent No.: US 9,962,246 B2
(45) Date of Patent: May 8, 2018

(54) METHOD AND DEVICE FOR APPLYING COLOR IN THE FIELD OF DENTAL TECHNOLOGY

(71) Applicant: PATIO-K AG, Schaanwald (LI)

(72) Inventor: Knut Miller, Schaanwald (LI)

(73) Assignee: Patio-K AG, Schaanwald (LI)

( * ) Notice: Subject to any disclaimer, the term of this patent is extended or adjusted under 35 U.S.C. 154(b) by 0 days. days.

(21) Appl. No.: 15/101,636

(22) PCT Filed: Dec. 8, 2014

(86) PCT No.: PCT/EP2014/003285
§ 371 (c)(1),
(2) Date: Jun. 3, 2016

(87) PCT Pub. No.: WO2015/082081
PCT Pub. Date: Jun. 11, 2015

(65) Prior Publication Data
US 2016/0302896 A1    Oct. 20, 2016

(30) Foreign Application Priority Data
Dec. 6, 2013    (DE) .......................... 10 2013 020 445

(51) Int. Cl.
*A61C 13/083*    (2006.01)
*A61C 13/00*    (2006.01)
(Continued)

(52) U.S. Cl.
CPC .............. *A61C 13/082* (2013.01); *A61C 5/77* (2017.02); *A61C 13/0004* (2013.01);
(Continued)

(58) Field of Classification Search
CPC ............................ A61L 27/32; A61C 13/0835
(Continued)

(56) References Cited

U.S. PATENT DOCUMENTS 4,064,311 A * 12/1977 McLean ............. A61C 13/0835
156/89.16
4,392,829 A * 7/1983 Tanaka ............... A61C 13/0003
433/208
(Continued)

FOREIGN PATENT DOCUMENTS

DE      4340252 A1    6/1995
DE    19922870 A1   12/2000
(Continued)

OTHER PUBLICATIONS

International Bureau of WIPO, International Preliminary Report on Patentability Issued in Application No. PCT/EP2014/003285, dated Jun. 7, 2016, WIPO, 16 pages.
(Continued)

*Primary Examiner* — Cachet I Sellman
(74) *Attorney, Agent, or Firm* — Fish & Richardson P.C.

(57) ABSTRACT

The invention relates to a method for applying color in the field of dental technology, including generating scan data by means of detecting the dental prosthesis using a scanner; computing an image of the dental prosthesis from the scan data; displaying the image, wherein the image is displayed as colored with a tooth color; receiving a user input; in response to the user input: a) applying the tooth color onto the dental prosthesis or onto a carrier foil for the dental prosthesis, or b) displaying the image, wherein the image is displayed as colored with a different tooth color, and receiving a further user input, wherein in response to the further user input, an application of the altered tooth color by means of a color application device onto the dental prosthesis, or onto the carrier foil for the dental prosthesis takes place.

12 Claims, 3 Drawing Sheets

Figure 1:
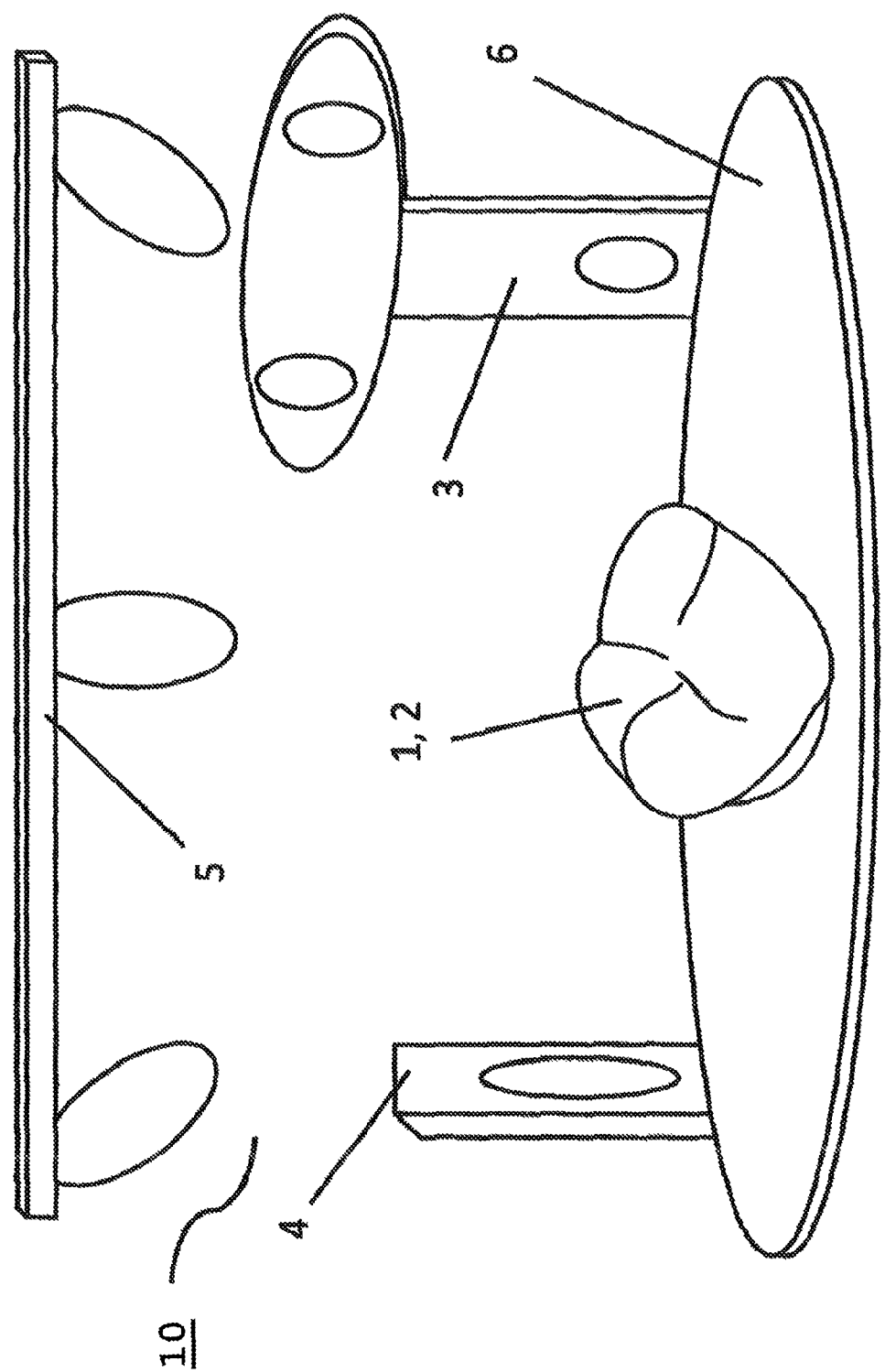

(51) Int. Cl.
*A61C 13/08* (2006.01)
*B05B 13/02* (2006.01)
*B05B 15/00* (2018.01)
*A61C 5/77* (2017.01)

(52) U.S. Cl.
CPC ........ *A61C 13/083* (2013.01); *B05B 13/0221* (2013.01); *B05B 15/00* (2013.01)

(58) Field of Classification Search
USPC .............................................. 427/2.26, 2.29
See application file for complete search history.

(56) References Cited

U.S. PATENT DOCUMENTS

| | | | | |
|---|---|---|---|---|
| 4,459,112 A | * | 7/1984 | Shoher .................... | A61C 5/77 433/218 |
| 4,676,751 A | * | 6/1987 | Shoher ............... | A61C 13/0003 428/607 |
| 4,940,637 A | * | 7/1990 | Shoher .................... | A61C 5/10 428/607 |
| 4,997,723 A | * | 3/1991 | Tanaka ................. | A61C 13/082 420/507 |
| 5,024,790 A | * | 6/1991 | Grossman .......... | A61C 13/0835 264/16 |
| 5,131,847 A | * | 7/1992 | Ijuin .................. | A61C 13/0003 433/223 |
| 5,186,626 A | * | 2/1993 | Tanaka ................... | A61C 13/26 433/180 |
| 6,426,149 B1 | * | 7/2002 | Machida .............. | A61C 13/082 428/434 |
| 6,481,353 B1 | * | 11/2002 | Geddes .................... | B41M 3/12 101/483 |
| 2002/0150859 A1 | * | 10/2002 | Imgrund .................. | A61C 7/00 433/24 |
| 2005/0074721 A1 | * | 4/2005 | Kim ..................... | A61C 13/083 433/208 |
| 2005/0170315 A1 | * | 8/2005 | Strobel .............. | A61C 13/0004 433/203.1 |
| 2008/0193899 A1 | | 8/2008 | Karlsson et al. | |
| 2011/0250566 A1 | * | 10/2011 | Yarovesky ......... | A61C 13/0835 433/212.1 |

FOREIGN PATENT DOCUMENTS

| | | |
|---|---|---|
| DE | 102007034005 A1 | 1/2009 |
| WO | 2009097288 A1 | 8/2009 |
| WO | 2013095968 A1 | 6/2013 |

OTHER PUBLICATIONS

ISA European Patent Office, International Search Report Issued in Application No. PCT/EP2014/003285, dated Apr. 2, 2015, IPO, 4 pages.

\* cited by examiner

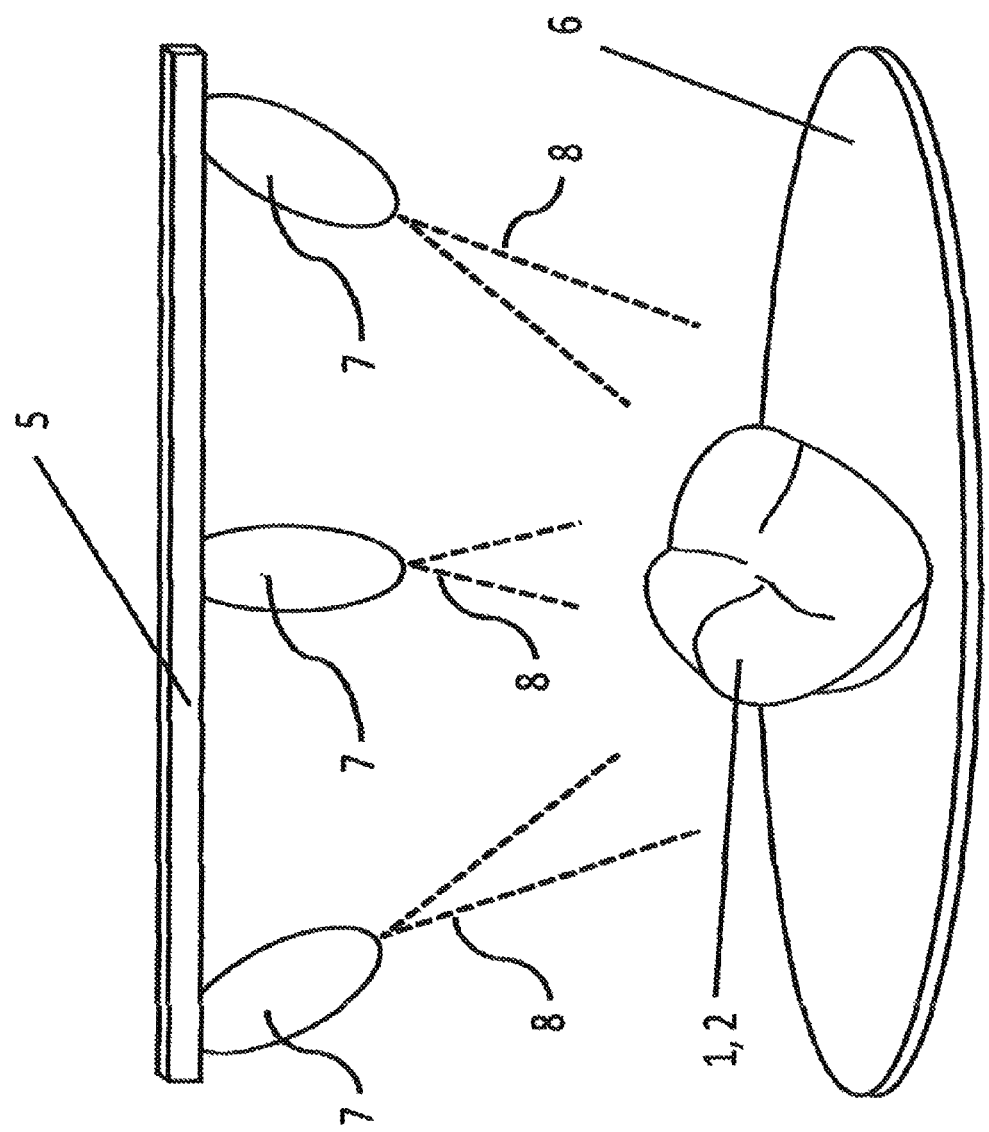

METHOD AND DEVICE FOR APPLYING COLOR IN THE FIELD OF DENTAL TECHNOLOGY

The invention relates to a method and a device for applying color in the field of dental technology.

In the state of art there are different methods and devices for coloring dental prosthesis such as, for example, ceramics. In dentistry besides the mechanical characteristics also the aesthetics is of crucial relevance.

Through a visual capturing or through selecting by means of standardized tooth shade guide or by means of electronic color capturing, such as color-measuring instrument the individual tooth color of the patient for dental restoration can be determined. These individual tooth colors are usually applied manually on the dental prosthesis by means of a brush or modeling instrument.

An individual coloring, which is carried out by applying a desired tooth color accurately is not possible with the known methods.

It is therefore, the object of the present invention to provide a method for applying color in the field of dental technology, in which the disadvantages of the prior art will be overcome.

This object is achieved by a method for applying color in the field of dental technology disclosed herein.

Furthermore, this object is achieved by a device for applying color in the field of dental technology disclosed herein.

Further advantageous embodiments of the present invention are specified elsewhere herein.

According to one aspect of the invention a method for applying color in the field of dental technology is provided, comprising the steps of:

Generating scan data by means of detecting the dental prosthesis by means of a scanner,
Calculating an image of the dental prosthesis from the scan data by means of a processing unit,
Representing the image by means of a display device, wherein the image is represented colored with a tooth color,
Receiving a user input by means of the processing unit,
In response to said user input:
a) Applying the tooth color by means of a color application device on the dental prosthesis or on the carrier foil for the dental prosthesis or
b) Displaying the image by the display device, wherein the image is represented colored with a modified tooth color and receiving a further user input, wherein in response to the further user input, an applying of the modified tooth color is carried out by means of a color application device on the dental prosthesis or on a carrier foil for the dental prosthesis.

Preferably, the scanner is a 3D scanner. By means of the 3D scanner scan data are generated. As part of a 3D scanning process the spatial dimensions for the dental prosthesis on a dental model, dental segment, or on natural teeth are determined directly on the patient. Preferably, the scan data are based on a prepared clinical situation in the mouth of a patient.

Preferably, the processing unit is a computer (personal computer). Preferably, the display device is a digital display device, more preferably, a screen of a computer (PC).

Preferably, the tooth color is represented visually by means of a CAD software program on a digital 3D dental prosthesis.

Preferably, the user input is carried out by an appropriate input on the computer. An input can be: "Yes" with the result that an application of the tooth color by means of a color application device should take place on the dental prosthesis or on a carrier foil for the dental prosthesis.

Receiving the user input by means of the processing unit triggers an appropriate response to the user inputs made.

Preferably, by means of the CAD software program the position and coloring of the determined tooth color on the dental prosthesis or the carrier foil can still be readjusted and modified at any time on the display device.

Thus, it is possible to select a completely different color and place it on the dental prosthesis or the carrier foil for the dental prosthesis.

An input can then alternatively be: "No" with the result that displaying the image takes place, wherein the image is represented colored with a modified tooth color and receiving a further user input takes place. Though, the further user input again takes place by an appropriate input on the computer. An input can be: "Yes" with the result that an application of the modified tooth color should take place by means of a color application device on the dental prosthesis or on the carrier foil for the dental prosthesis.

If an input will again be "No", the procedure is repeated as just described.

Thus, an individual coloring of the dental prosthesis or of a foil for the dental prostheses is provided.

Particularly preferably, the color application device is a spraying device with nozzles. Preferably, the nozzles are individually controllable in order to allow a targeted color application. A positioning of the nozzles is adjusted by means of a software program corresponding to the surface structure of the dental prosthesis.

In a further preferred embodiment of the invention the tooth color is sprayed or printed along a defined region on the dental prosthesis or on the carrier foil for the dental prosthesis in response to an additional user input by means of the color application device.

Preferably, the response to an additional user input takes place after the steps a) and b).

Based on the shape or rather surface structure of the dental prosthesis it is possible to apply the color in correct position.

Preferably, this way also an iridescent application of color on the dental prosthesis can be accomplished.

In this way an individual coloring with an accurate application of a desired tooth color is feasible.

In a preferred embodiment of the invention, the method further comprises the following step of:

Determining a tooth color for a dental prosthesis by means of a color-measuring instrument or by means of a tooth shade guide for the colored representation of the image.

Though, the individual tooth color of the patient can be determined by visual detecting or selecting based on standardized tooth shade guides or by means of electronic color-measuring instruments.

In a further preferred embodiment of the invention the carrier foil is made from a foil based on the scan data by means of a punching or cutting device.

With that said the shape of the foil can be calculated accurately and adapted respectively to the desired tooth shape or dental prosthesis.

Preferably, the carrier foil is punched, cut or pressed out of the film.

In a further preferred embodiment of the invention, the method further comprises the following step of:

Positioning the dental prosthesis or the carrier foil by means of a positioning device.

With that said the dental prosthesis or the carrier foil can be fixed on the positioning device for detecting the dental prosthesis and the application of color by means of the color application device.

In a further preferred embodiment of the invention the method further comprises one of the following steps of:

Fixing the tooth color applied directly on the dental prosthesis by means of a firing process or by means of a polymerization process, Fixing the tooth color applied on the carrier foil on the dental prosthesis by means of a firing process or Fixing the tooth color applied on the carrier foil on the dental prosthesis by means of a polymerization process.

Preferably, the firing process is employed on a dental prosthesis made of ceramics in order to fix the applied tooth color on the dental prosthesis.

Preferably, the carrier foil is a foil for applying on the dental prosthesis.

Preferably, the carrier foil is a transparent foil that has been previously colored or on which color was applied or sprayed.

Particularly preferably, the firing process is employed on a dental prosthesis made of ceramics in order to fix the applied tooth color from the carrier foil on the dental prosthesis.

Preferably, the carrier foil is dissolved without trace as a result of the firing process such as only the tooth color remains on the dental prosthesis.

In this way it is possible to accomplish a color application without foil residues on the dental prosthesis.

Particularly preferably, the polymerization process is employed on a dental prosthesis that is not made of ceramics in order to fix the applied tooth color from the carrier foil on the dental prosthesis. Preferably, the foil is polymerized during the polymerization process without trace such as only the tooth color remains on the dental prosthesis.

In this way it is also possible to accomplish a color application without foil residue on the dental prosthesis.

Particularly preferably, a clear coat or a glaze is applied on a finished fired or finished polymerized dental prosthesis to protect the colors on the dental prosthesis.

According to a further aspect of the invention, a device is provided for applying color in the field of dental technology comprising:

a scanner configured to generate scan data by means of detecting a dental prosthesis, a processing unit configured to calculate an image of the dental prosthesis based on the scan data, a display device configured to represent the image, wherein the image is represented colored with a tooth color, wherein the processing unit is further configured to receive an user input, wherein in response to user input
a) by means of a color application device the tooth color is applied on the dental prosthesis or on a carrier foil for the dental prosthesis or
b) the display device is configured to represent the image, wherein the image is represented colored with a modified tooth color, wherein in response to a further user input by means of a color application device the tooth color is applied on the dental prosthesis or on the carrier foil for the dental prosthesis.

Preferably, the scanner is a 3D scanner. By means of the 3D scanner scan data are generated. As part of a 3D scanning process the spatial dimensions for the dental prosthesis on a dental model, dental segment, or on natural teeth are determined directly on the patient. Preferably, the scan data are based on a prepared clinical situation in the mouth of a patient.

Preferably, the processing unit is a computer (personal computer). Preferably, the display device is a digital display device, more preferably, a screen of a computer (PC).

Preferably, the tooth color is represented visually by means of a CAD software program on a digital 3D dental prosthesis.

Preferably, by means of the CAD software program the position and coloring of the determined tooth color on the dental prosthesis or the carrier foil can still be readjusted and modified at any time on the display device.

Thus, it is possible to select a completely different color and place it on the dental prosthesis or the carrier foil for the dental prosthesis.

Particularly preferably, the color application device is a spraying device with nozzles. Preferably, the nozzles are individually controllable in order to allow a targeted color application. A positioning of the nozzles is adjusted by means of a software program corresponding to the surface structure of the dental prosthesis.

Thus, an individual coloring of the dental prosthesis or of a foil for the dental prostheses is provided.

In a further preferred embodiment of the invention the dental prosthesis is producible in the desired shape and color by means of a 3D printer.

In a further preferred embodiment of the invention the device further comprises a positioning device configured to position the dental prosthesis or the carrier foil.

This makes it possible to position the dental prosthesis or the carrier foil for the color application accordingly and apply the color in a simple manner.

In a further preferred embodiment of the invention the dental prosthesis is a prosthesis, an implant, a bridge, a crown, a dental crown, a partial crown or a veneer.

Preferably, bridges consist of abutments (fixing elements) and of bridge bodies (bridge members). Bridges can be made of metal, ceramics or the combination of both materials as well as ceromer, plastics, plastics on metal or composites and are fixable on the corresponding prepared (ground) anchorage teeth by means of a special cement.

Preferably, a dental crown covers completely the respective tooth (like a thimble). Besides, there are also partial crowns that do not cover completely the respective tooth.

Preferably, an implant is a dental root replacement on which a crown or a removable dental prosthesis is attached. The function of implants corresponds to the ones of natural teeth in this context. Therefore, they are applicable as abutments as well as holding and supporting elements in combined dental prosthesis. An implant can also be indicated when a single tooth is missing, the neighboring teeth are healthy and should not be prepared, i.e. ground for the recording of a bridge. Though, the dental implant is crowned with a single crown.

Preferably, a prosthesis denotes the replacement of teeth by artificially created, functionally similar products.

Preferably, a veneer is a thin, translucent ceramic layer for the teeth, which is glued on the tooth surface with a special glue.

In a further preferred embodiment of the invention, the dental prosthesis is a ceramic or consists of a high-strength plastic. Preferably, the ceramic is a glas-, feldspar-, lithium-, lithium disilicate-, or oxide ceramics. Particularly preferred, the ceramic is a metal ceramics or a faced metal ceramics.

Preferably, the ceramic is pre-sintered ceramic, which means that a ceramic mold that has been treated thermally at least once but has not been finally sintered yet. Particularly preferred, the ceramic is finally sintered in a ceramic furnace.

Particularly preferred, the ceramic is a producible press-ceramic by means of a press process.

Preferably, the plastics consist of acryl, PMMA or ceromer. Preferably, the plastic is a ceramic infiltrated composite, a hybrid ceramic or consist of various composites.

In a further preferred embodiment of the invention, the carrier foil is a foil for applying on the dental prosthesis.

Preferably, the carrier foil is a transparent foil that is to be colored.

Particularly preferred, the carrier foil is configured to dissolve without trace as a result of a firing process or cure as a result of a polymerization process.

In this way it is possible to accomplish a color application without foil residue on the dental prosthesis.

Preferably, the carrier foil is flexibly shapeable.

Particularly preferred, the carrier foil has a thickness of a few pm-meters.

In a particularly preferred embodiment of the invention, a punching or cutting device is provided that is configured to produce the carrier foil based on the scan data.

This way it is possible to mold the constructed carrier foil according to the shape of the dental prosthesis. Preferably, the carrier foil is applied to the dental prosthesis before sintering.

Further advantages and details of the invention are exemplified on the basis of the embodiments as shown in the figures.

The Figures show in detail:

FIG. 1 a schematic view of a detection-and color application device according to a device of the invention for the field of dental technology.

Figure 2:
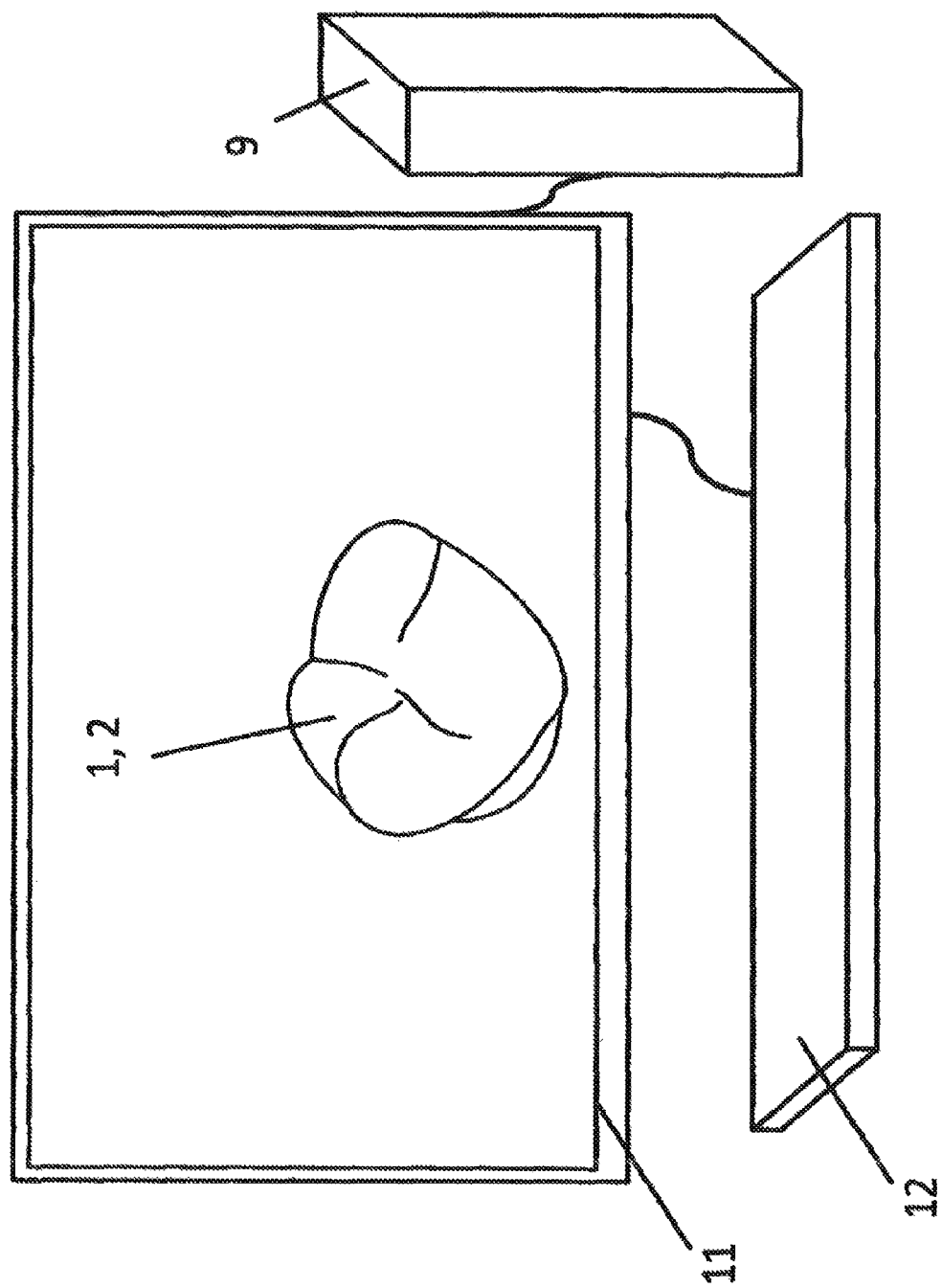

FIG. 2 a schematic view of a display device with a processing unit according to a device of the invention for the field of dental technology.

FIG. 3 a schematic view of a color application device of FIG. 1 in operation.

In FIG. 1 a schematic view of a detection-and color application device according to a device of the invention for the field of dental technology is shown.

The device 10 comprises a 3D scanner 3, a color-measuring instrument 4, a color application device 5 and a positioning device 6. The 3D scanner 3, the color-measuring instrument 4 and the color application device 5 are formed as individual parts of the device 10.

The color-measuring device 4 is configured to determine the color of the dental prosthesis 1. The 3D scanner 3 is configured to detect the dental prosthesis 1 spatially. The color application device 5 is configured to apply the desired tooth color directly on the dental prosthesis 1. The positioning device 6 is configured to position a dental prosthesis 1.

In FIG. 2 a schematic view of a display device with a processing unit according to a device of the invention for the field of dental technology is shown.

The device 10 further comprises a processing unit 9, a display device 11 as well as an operating unit 12 for input of user inputs (commands) to the processing unit 9.

First, scan data are generated by means of detecting the dental prostheses 1 by means of 3D scanners 3, wherein the dental prosthesis 1 is fixed on the positioning device 6. As part of the 3D scan process the scan data (spatial dimensions) are determined for the dental prosthesis 1.

It follows a calculating of an image of the dental prosthesis 1 from the scan data by means of a processing unit 9. This is followed by representing the image, wherein the image is represented colored with a tooth color on the display device 11, a screen; which means that the tooth color is visually represented on a digital 3D dental prosthesis by means of a CAD software program.

Upon receiving of a user input by means of the processing unit 9, in response to the user input an application of the tooth color follows by means of the color application device 5 on the dental prosthesis 1. Optionally, modifying the color as part of a further user input is also possible.

The dental prosthesis 1 is formed as a dental crown. The dental prosthesis 1 consists of a high-strength plastic, particularly veneer, partial crown, inlay, onlay, implant, partial prosthesis or bridge and total prosthesis.

Alternatively, a carrier foil 2 is provided for the dental prosthesis 1, which can be applied on the dental prosthesis 1. Based on the 3D scans the restoration area can be defined automatically or individually digital, which is to be covered with the carrier foil. Restoration area is defined digitally colored based on digital color-measuring instruments, on the commercially available tooth shade guides, or on a partial- or completely single individual color by means of a software program.

Based on the restoration area, the geometry and the color of the carrier foil 2 are defined. The carrier foil 2 has thereby, the geometry of the dental prosthesis 1.

The carrier foil 2 is a transparent foil that can be colored by means of the color application device 5 and that has a thickness of a few pm-meters.

By means of a punching or cutting device the carrier foil 2 is producible based on the determined values of the 3D scan process or construction process.

In FIG. 3 a schematic view of a color application device o FIG. 1 in operation is shown.

In contrast to FIG. 1, as a matter of clear view, the representation of the 3D scanner 3 as well as of the color-measuring instrument 4 is omitted.

The color application device 5 has a plurality of nozzles 7, of which three nozzles are illustrated. The nozzles 3 are positioned in such a way towards the dental prosthesis 1 or the carrier foil 2 so that color 8 can be applied on the dental prosthesis 1 or on the carrier foil 2. A positioning of the nozzles is adjustable by means of software programs corresponding to the surface structure of the dental prosthesis 1 or the carrier foil 2.

Below, the whole process in relation to a carrier foil is illustrated:

First, scan data are generated by means of detecting the dental prostheses 1 by means of 3D scanners 3 or an intraoral scanner, wherein the dental prosthesis 1 is fixed on the positioning device 6. As part of the 3D scan process or intraoral scanner the scan data (spatial dimensions) are determined for the dental prosthesis 1.

It follows a calculating of an image of the dental prosthesis 1 from the scan data by means of a processing unit 9.

Based on the 3D scans the restoration area can be defined automatically or individually digital, which is to be covered with the carrier foil.

This is followed by representing the image, wherein the image is represented colored with a tooth color (on the display device) or the tooth color can be defined and inserted manually; which means that the tooth color is visually represented on a digital 3D dental prosthesis by means of a CAD software program.

A restoration area is defined colored based on digital color-measuring instruments, on the commercially available tooth shade guides, or on a partial- or completely single individual color by means of a software program.

Based on the restoration area, the geometry and the color of the carrier foil are defined.

The carrier foil is a transparent foil that can be colored by means of the color application device and that has a thickness of a few pm-meters.

Upon receiving of a user input by means of the processing unit 9, in response to the user input an application of the tooth color follows by means of the color application device 5 on the carrier foil. Optionally, modifying the color as part of a further user input is also possible and if applicable, based on a color software for individual coloring.

By means of a punching or cutting device the carrier foil 2 is producible based on the determined values of the 3D scan process or construction process.

The application of the carrier foil on the dental prosthesis is carried out manually, which means extra-oral and/or intra-oral.

Thereupon, the carrier foil is either burned up, preferably without residues combustible or cured by a polymerization process.

When burning up the carrier foil, for example, on ceramics a ceramic glaze for protecting the colors can be applied in the same or in a separate step of procedure.

During polymerization process, if necessary, pressure-, light-, temperature-, or rather combination of these polymerization processes a protective layer for the colors can be applied in the same or in a separate step of procedure.

With the invention, an individual coloring of dental prosthesis or of carrier foil for dental prosthesis is possible, in which an accurate application of a desired tooth color takes place.

LIST OF REFERENCE CHARACTERS

1 Dental prosthesis
2 Carrier foil
3 3D scanner
4 Color-measuring instrument
5 Color application device
6 Positioning device
7 Nozzles
8 Color
9 Processing unit
10 Device
11 Display device
12 Operation unit

The invention claimed is:

1. A method for applying color in the field of dental technology comprising the steps of:
generating scan data by means of detecting a dental prosthesis by means of a scanner,
calculating an image of the dental prosthesis from the scan data by means of a processing unit,
representing the image by means of a display device, wherein the image is represented colored with a tooth color,
receiving a user input by means of the processing unit, in response to said user input:
a) applying the tooth color by means of a color application device on carrier foil for the dental prosthesis or
b) displaying the image by the display device, wherein the image is represented colored with a modified tooth color and receiving a further user input, wherein in response to the further user input, an applying of the modified tooth color is carried out by means of a color application device on a carrier foil for the dental prosthesis, wherein the carrier foil, based on the scan data, is made from a foil by means of a punching or cutting device; and
applying the carrier foil with the tooth color to the dental prosthesis.

2. The method according to claim 1, wherein in response to an additional user input the tooth color is sprayed or printed along a defined region on the carrier foil for the dental prosthesis by means of the color application device.

3. The method according to claim 1, further comprising the following step of: determining a tooth color for a dental prosthesis by means of a color-measuring instrument or by means of a tooth shade guide for the representation of the image.

4. The method according to claim 1, further comprising the following step of: positioning the dental prosthesis or the carrier foil by means of a positioning device.

5. The method according to claim 1, further comprising the following steps of:
fixing the tooth color applied on the carrier foil on the dental prosthesis by means of a firing process or
by means of a polymerization process.

6. The method according to claim 1, wherein the carrier foil is a transparent foil.

7. The method according to claim 1, further comprising dissolving the carrier foil leaving the tooth color on the dental prosthesis.

8. A device for applying color in the field of dental technology comprising:
a scanner configured to generate scan data by means of detecting a dental prosthesis,
a processing unit configured to calculate a visual 3D image of the dental prosthesis based on the scan data,
a display device configured to represent the image, wherein the image is represented colored with a tooth color,
a punching or cutting device configured to make carrier foil based on the scan data,
wherein the processing unit is further configured to receive an user input, wherein in response to user input
a) by means of a color application device the tooth color is applied on the carrier foil for the dental prosthesis before the carrier foil is applied to the dental prosthesis or
b) the display device is configured to represent the image, wherein the image is represented colored with a modified tooth color, wherein in response to a further user input by means of a color application device the tooth color is applied on the carrier foil for the dental prosthesis before the carrier foil is applied to the dental prosthesis, wherein the carrier foil, based on the scan data, is made from a foil by means of a punching or cutting device.

9. The device according to claim 8, wherein the device further comprises a positioning device configured to position the dental prosthesis or the carrier foil.

10. The device according to claim 8, wherein the dental prosthesis is a bridge, a dental crown, an implant, a prosthesis, a prosthetic treatment or a veneer.

11. The device according to claim 8, wherein the dental prosthesis is a ceramic or consists of a high-strength plastic.

12. The device according to claim 8, wherein the carrier foil is a foil for applying on the dental prosthesis.

\* \* \* \* \*